United States Patent
Kaes et al.

(10) Patent No.: US 7,833,245 B2
(45) Date of Patent: Nov. 16, 2010

(54) INTERVERTEBRAL IMPLANT WITH MOVEMENT RESISTANT STRUCTURE

(75) Inventors: David R. Kaes, Toms River, NJ (US); John W. Morris, Beechwood, NJ (US); Lawrence A. Shimp, Morganville, NJ (US); John Winterbottom, Jackson, NJ (US); Fred Geisler, Aurora, IL (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 10/483,804

(22) PCT Filed: Jul. 12, 2002

(86) PCT No.: PCT/US02/22138

§ 371 (c)(1), (2), (4) Date: Aug. 5, 2004

(87) PCT Pub. No.: WO03/005938

PCT Pub. Date: Jan. 23, 2003

(65) Prior Publication Data

US 2004/0249377 A1  Dec. 9, 2004

Related U.S. Application Data

(60) Provisional application No. 60/304,896, filed on Jul. 12, 2001.

(51) Int. Cl.
*A61B 17/70* (2006.01)
*A61F 2/44* (2006.01)

(52) U.S. Cl. .................... 606/246; 623/17.11

(58) Field of Classification Search .................. 606/61, 606/69, 70, 71; 623/17.11, 17.12, 17.13, 623/17.14, 17.15, 17.16
See application file for complete search history.

(56) References Cited

U.S. PATENT DOCUMENTS

| | | | | | |
|---|---|---|---|---|---|
| 4,743,256 | A | * | 5/1988 | Brantigan | .................... 128/898 |
| 5,514,180 | A | * | 5/1996 | Heggeness et al. | ....... 623/17.16 |
| 5,707,962 | A | * | 1/1998 | Chen et al. | .................... 514/12 |
| 5,814,084 | A | * | 9/1998 | Grivas et al. | ............. 623/23.48 |
| 5,888,223 | A | * | 3/1999 | Bray, Jr. | ................... 623/17.16 |
| 5,989,289 | A | * | 11/1999 | Coates et al. | ............ 623/17.16 |
| 6,033,438 | A | * | 3/2000 | Bianchi et al. | ........... 623/17.16 |
| 6,066,175 | A | * | 5/2000 | Henderson et al. | ....... 623/17.11 |
| 6,096,080 | A | | 8/2000 | Nicholson et al. | |
| 6,096,081 | A | * | 8/2000 | Grivas et al. | ............. 623/17.11 |
| 6,106,557 | A | * | 8/2000 | Robioneck et al. | ....... 623/17.15 |

(Continued)

FOREIGN PATENT DOCUMENTS

EP   1099428   5/2001

(Continued)

*Primary Examiner*—Thomas C Barrett
*Assistant Examiner*—Nicholas Woodall
(74) *Attorney, Agent, or Firm*—Kenneth E. Levitt; Dorsey & Whitney LLP

(57) ABSTRACT

An implant unit used in surgery has a body made from osteogenic implantable material and including an implant portion and a retaining portion, which is coupled to and extends transversely to the implant portion. The retaining portion is attached to the sidewall of the adjoining vertebral body or mammal bone to prevent displacement of the implant portion relative to the vertebral body or mammal bone and to accelerate fusion therebetween.

24 Claims, 10 Drawing Sheets

U.S. PATENT DOCUMENTS

| | | | |
|---|---|---|---|
| 6,120,503 A * | 9/2000 | Michelson | 606/61 |
| 6,156,037 A * | 12/2000 | LeHuec et al. | 606/61 |
| 6,206,922 B1 * | 3/2001 | Zdeblick et al. | 623/17.11 |
| 6,206,923 B1 | 3/2001 | Boyd et al. | |
| 6,210,442 B1 * | 4/2001 | Wing et al. | 623/17.11 |
| 6,231,610 B1 * | 5/2001 | Geisler | 623/17.11 |
| 6,235,034 B1 * | 5/2001 | Bray | 606/71 |
| 6,235,059 B1 * | 5/2001 | Benezech et al. | 623/17.16 |
| 6,264,655 B1 * | 7/2001 | Pisharodi | 606/61 |
| 6,306,170 B2 * | 10/2001 | Ray | 623/17.11 |
| 6,325,827 B1 * | 12/2001 | Lin | 623/17.16 |
| 6,328,738 B1 * | 12/2001 | Suddaby | 606/57 |
| 6,364,881 B1 * | 4/2002 | Apgar et al. | 606/69 |
| 6,395,030 B1 * | 5/2002 | Songer et al. | 623/17.11 |
| 6,432,106 B1 * | 8/2002 | Fraser | 606/61 |
| 6,562,073 B2 | 5/2003 | Foley | |
| 6,569,168 B2 | 5/2003 | Lin | |
| 6,576,017 B2 * | 6/2003 | Foley et al. | 623/17.16 |
| 6,666,866 B2 | 12/2003 | Martz et al. | |
| 6,682,563 B2 * | 1/2004 | Scharf | 623/17.16 |
| 6,730,127 B2 * | 5/2004 | Michelson | 623/17.16 |
| 6,746,454 B2 | 6/2004 | Winterbottom et al. | |
| 6,837,905 B1 * | 1/2005 | Lieberman | 623/17.16 |
| 6,911,045 B2 | 6/2005 | Shimp | |
| 2001/0032017 A1 * | 10/2001 | Alfaro et al. | 623/17.11 |
| 2002/0082597 A1 * | 6/2002 | Fraser | 606/61 |
| 2002/0107571 A1 * | 8/2002 | Foley | 623/17.11 |
| 2002/0128655 A1 * | 9/2002 | Michelson | 606/70 |
| 2003/0130667 A1 | 7/2003 | Lin | |
| 2004/0010254 A1 * | 1/2004 | Cook et al. | 606/61 |
| 2004/0098129 A1 | 5/2004 | Lin | |
| 2004/0162562 A1 | 8/2004 | Martz | |
| 2004/0243242 A1 | 12/2004 | Sybert et al. | |
| 2005/0038511 A1 | 2/2005 | Martz et al. | |
| 2005/0240188 A1 | 10/2005 | Chow et al. | |
| 2005/0251146 A1 | 11/2005 | Martz et al. | |
| 2006/0095043 A1 | 5/2006 | Martz et al. | |
| 2006/0149376 A1 | 7/2006 | Shimp et al. | |
| 2007/0073293 A1 | 3/2007 | Martz et al. | |

FOREIGN PATENT DOCUMENTS

| | | |
|---|---|---|
| WO | 99/52473 | 10/1999 |
| WO | 01/49220 | 7/2001 |
| WO | 01/66028 | 9/2001 |

* cited by examiner

INTERVERTEBRAL IMPLANT WITH MOVEMENT RESISTANT STRUCTURE

CROSS REFERENCE TO RELATED APPLICATION

This application claims priority from Provisional Application Ser. No. 60/304,896 filed Jul. 12, 2001 and fully incorporated herein by reference.

BACKGROUND

1. Technical Field

The present disclosure relates generally to an implant for insertion into a receiving bed formed between adjoining vertebrae. Particularly, the invention relates to an intervertebral implant adapted to fuse with the adjoining vertebrae and including a movement resistant structure for preventing relative motion between the intervertebral implant and the adjoining vertebrae during the period required for fusion.

2. Background of Related Art

Surgical implants are well known in the art for treatment of the spine for deficiencies including disease, trauma, deformity, and/or degenerative spinal conditions. The purpose of the implant is to reinforce and fuse with the spine by use of strategically placed attachment tools or implants. When a segment of the human spine degenerates, or otherwise becomes diseased, it may become necessary to surgically remove the affected disc of that segment, and to replace portions of it for the purpose of obtaining a spinal fusion. The implant primarily functions to restore a more normal, pre-morbid spatial relationships, and provide enhanced stability and support across affected segments.

Generally, implants suitable for intervertebral implantation facilitate fusion of adjoining vertebrae and include movement resistant structures that, add strength and/or prevent expulsion of the implant from the intervertebral space during fusion process.

Intervertebral implants are available in a variety of different shapes including cylindrical dowels, tapered wedges, rectangular blocks, etc. For example, cylindrical dowels may be threaded to retain the implant within the intervertebral space. Alternately, intervertebral implants may include surface ridges, grooves, or protrusions to prevent movement of the implant in relation to the adjoining vertebrae. Structures designed to prevent relative movement between the implant and engaged spinal elements may not always be effective. Thus, spinal fusion procedures may fail due to movement of the implant in relation to the adjoining vertebrae during the fusion process.

There are several approaches for accessing the spinal disc space, typically the spine is approached from the anterior, anterior lateral, lateral, posterior lateral or the posterior direction. The lateral approach is often preferred due to the ease with which the spinal cord, dural sac, major vessels and nerve roots can typically be avoided.

In entering the disc space anteriorly, a very important stabilizing structure, the anterior longitudinal ligament, is compromised. This structure physiologically acts as a significant restraint, resisting the anterior displacement of the disc itself and acting as a tension band binding the front portions of the vertebrae so as to limit spinal hyperextension.

Historically, various devices have been utilized in an attempt to compensate for the loss of this important stabilizing structure. These devices have assumed the form of blocks, bars, cables, plates or some combination thereof, and are bound to the vertebrae by screws, staples, bolts, or some combination thereof. The earliest examples are of a metal plate attached to adjacent vertebrae with course-threaded screws. The following documents illustrate some of the approaches known in the art.

U.S. Pat. No. 4,743,256 discloses the use of a block inserted to replace the disc, affixed to a plate then screwed to the vertebrae above and below.

U.S. Pat. No. 4,401,112 discloses the use of a turnbuckle affixed to an elongated staple such that at least one entire vertebral body is removed, the turnbuckle portion is placed within the spine, and the staple extends both above and below the turnbuckle and engages the adjacent vertebrae to the one removed.

U.S. Pat. No. 6,066,175 discloses a titanium implant assembly having an integrally formed implant and retaining portions.

A unit including separate implant and retaining parts, particularly those made from metal, is so positioned upon its insertion into the intervertebral space so that the retaining portion tends to support a significant portion of spinal loads. Such an uneven distribution of loads causes gradual loosening of the fasteners traversing the retaining portion that attach to the vertebrae.

The retaining portion of known implant assemblies typically has a continuous, flat surface extending complementary to the opposing surface of the spine. But for the fasteners attaching the retaining part to the vertebrae, the retaining part does not have any additional load-bearing surface capable taking loads imposed on the spine. As a consequence, known structures of retaining plates have limited contact areas between the implant and the bony mass of the spine.

A metallic implant always remains a foreign body, which is not able to accurately mimic the biomechanical or biological characteristics of the spine. Although such a metallic implant often consists of an internal graft promoting incorporation and growth of new bone tissue as a result of its osteoconductive capabilities, metallic parts consisting of a cage and a retaining portion do not promote wound healing and/or remodeling of new bone. A large part of the metallic implant never fuses with the adjoining bone and never is replaced by host bone and, thus, will never recover its original, natural qualities. Furthermore, a subsequent surgery is often required to remove the retaining portion of the construct. Since a large area between the metallic implant and the adjacent bone is not capable of fusion, relative motion between the bone and implant may cause gradual loosening of fasteners, which, in turn, leads to undesirable implant mobility. Under certain circumstances such a phenomenon may lead to neural damage, vascular damage and/or bleeding.

Accordingly, there is a need for an improved implant, which allows the implant as a whole to fuse with the adjoining bone and to enable promotion of bone growth. Furthermore, it is desirable to provide an intervertebral implant having more effective movement resistant structure to prevent relative displacement between an intervertebral implant unit and vertebrae during the period required for successful fusion.

OBJECTS OF THE INVENTION

It is, therefore, an object of the present invention to provide an implant unit capable of supporting loads and, in a preferred embodiment, through its bone healing activity. Inherent in this activity, is the implant's ability to incorporate medically/surgically useful substances to a surgical site, promote and/or accelerate new bone growth.

Still another object of the invention is to provide an implant unit, and particularly an intervertebral implant unit including an implant portion and a retaining portion, both of which incorporate substances capable of fusing with the adjoining vertebrae while preventing relative motion between the implant unit and the adjoining vertebrae during the period required for fusion.

Yet another object of the invention is to provide a bone implant unit including a retaining portion having an increased contact area with adjacent bone to facilitate gradual transfer of loads from the retaining portion to newly formed bone tissue during the period required for fusion.

A further object of the invention is to provide a monolithic implant unit including an implant portion and a retaining portion made from material having osteogenic capabilities and capable of incorporating, remodeling and, ultimately, fusing with the adjoining bone.

Still a further object of the invention is to provide an improved method for discectomy that minimizes site-related complications and limits relative motion between an implant unit and adjoining vertebrae to provide successful fusion therebetween.

Another object of the invention is to provide an implant assembly featuring a simple and reliable coupling system that allows the implant portion and the retaining portion to be detachably engaged with one another and also with the adjoining bone.

SUMMARY OF THE INVENTION

In accordance with one aspect of the invention, the implant construct is formed or assembled as a monolithic or one-piece unit including an implant portion and a retaining portion. The retaining portion extends transversely to the implant portion and is attached with fasteners to the adjoining bone. Since the retaining portions and implant portions are rigidly coupled, the retaining portion of the implant construct minimized motion of the construct relative to adjacent bone structures, thus enhancing the likelihood of successful fusion.

According to another aspect of the invention, the entire implant, including the transversely extending portion and the retaining portions is made up of materials that provide a osteogenic, osteoconductive and/or osteoinductive effect. This lead to an effective fusion between the implant and adjoining bone without the need for removing the retaining portion after the fusion has been completed.

The term "osteogenic" as applied to the osteoimplant of this invention shall be understood as referring to the ability of the osteoimplant to enhance or accelerate the ingrowth of new bone tissue by one or more mechanisms such as osteogenesis, osteoconduction and/or osteoinduction.

The term "bone repair site" is understood refer to one resulting from injury, defect brought about during the course of surgery, infection, malignancy or developmental malformation, which requires mechanical support.

The term "osteoconduction" as used herein shall be understood to refer to the ability of a substance or material to provide biologically inert surfaces which are receptive to the growth of new host bone.

The term "osteoinduction" as used herein shall be understood to refer to the ability of a substance to recruit cells from the host which have the potential for repairing bone tissue.

According to still another aspect of the invention, the bone implant is advantageously utilized for treating traumas or degenerative changes of the spine. In particular, an intervertebral monolithic implant has an implant portion shaped to correspond to a variety of anatomic configurations of the disc space. The retaining portion, which is formed integrally with the implant portion and extends along the spine and is attached thereto so as to reduce axial and torsional loads imposed on the implant portion. As a result, the inserted monolithic implant unit provides improved segment stability.

According to another aspect of the invention, the bone implant is advantageously utilized for treating bone defects, e.g., defects caused by injury, surgery, infection, malignancy, and/or developmental malformation. The entire implant, suitably sized and shaped, can be utilized as a graft or replacement in a wide variety of orthopaedic, neurosurgical and oral and maxillofacial surgical procedures. These procedures include, but are not limited to: repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. Specific bones which can be repaired or replaced with the bone-derived implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

In particular, while the implant portion of the inventive implant unit supports loads and provides a scaffold for healing, the retaining portion, made preferably from bone and bone related materials, helps to keep the implant in place and the bone ends aligned. One of the advantages of such a biomechanical structure is that the retaining portion does not have be removed (in a second operation) while metal plates often require removal after healing is completed.

A further aspect of the invention is concerned with material suitable for manufacturing the inventive implant unit. Preferably, the inventive implant unit is made from bone consisting of a biocompatible material obtained from human and animal tissues, plants, and insects. These biocompatible materials include, but are not limited to, bone, partially demineralized bone, demineralized bone, tendon, ligament, collagen, elastin, reticulin, cellulose, algininc acid, chitosan, small intensine subcumosa, silk, biocompatible polymers and mixtures thereof. The material can also be obtained from microorganisms, particularly genetically engineered microorganisms such as yeast and bacteria and other materials, as disclosed in U.S. Pat. Nos. 5,243,038 and 5,989,894, each incorporated herein by reference.

Yet another aspect of the invention provides for improved geometry of a retaining portion having an attaching surface formed with a ledge to increase a contact area between the implant unit, in particular the intervertebral implant unit, and the adjoining bone sidewall. As a consequence of the increased contact area, the growth of the inventive implant unit into the adjoining bone, in a preferred embodiment the adjoining vertebrae, is accelerated while spinal stability is enhanced.

In accordance with a further aspect of the present invention, a new method, particularly a method for cervical, thoracic and/or lumbar discectomy and fusion, consists of cutting recesses into the vertebral bodies and juxtaposing the recessed surfaces with respective surfaces of the implant.

This creates a large contact area between the implant unit and biologically active bone, thus facilitating fusion while improving spinal stability.

BRIEF DESCRIPTION OF THE DRAWINGS

The above and other objects, features and advantages the following drawings, in which.

DETAILED DESCRIPTION OF PREFERRED EMBODIMENTS

Figure 5:
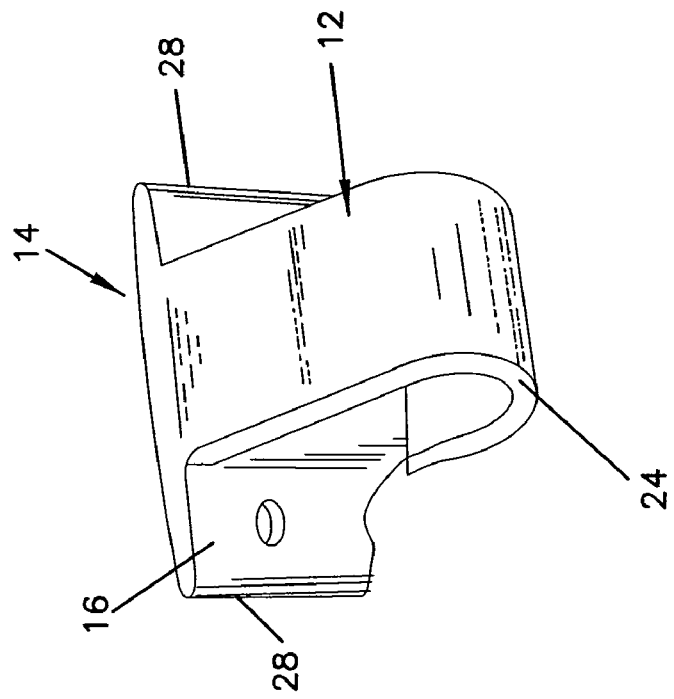
FIG. 5 is an isometric view of a further embodiment of the implant unit manufactured in accordance with the invention.

Preferred embodiments of the presently disclosed intervertebral implant unit with movement resistant structure will now be described in detail with reference to the drawings, in which like reference numerals designate identical or corresponding elements in each of the several views.

Referring to FIGS. 1A-1D, the inventive monolithic implant unit can have a variety of configurations adapted to provide new bone ingrowth and fusion of human or animal bones by one or more biological mechanisms. These mechanisms include chondrogenesis, osteogenesis, osteoconduction and/or osteoinduction that ultimately leads to complete fusion of the implant to adjoining bone structures. Although the following discussion is mostly concentrated on disclosing anterior and lateral cervical, thoracic, and lumber implants/instrumentation, the inventive concept can be easily adopted to a variety of surgical procedures providing immediate biomechanical stability to various bone structures and/or joints.

Particularly, the presently disclosed implant units each include a body 10 and having an implant portion 12 and a retaining portion 14, which can be detachably coupled to one or, preferably, formed as a one-piece component or as a monolithic body. The body 10 is preferably made from demineralized human and animal bones including cancellous bone, cortical bone, and/or bone composites, as disclosed below. Accordingly, while the implant portion 12 is being reliably fused with the adjoining bone, the retaining portion 14, which extends transversely to the insertion plane of the implant portion and has an end 25, is both biocompatible with the sidewall of the adjoining bone and is reliably attached thereto. As a consequence, the use of the retaining portion 14 made from materials exhibiting osteogenic characteristics improves attachment of the inventive implant to the adjoining bone and eliminates the need for a subsequent surgery typically directed to removing the retaining portion after the fusion has been completed.

Human or animal bone is a connective tissue having numerous collagen fibers, which are incorporated in an intervening matrix impregnated with calcium phosphate material. Collagen fibers give the bone tensile strength, whereas calcium phosphates provide compressive strength. Allograft bone tissue is widely used in orthopedic and neurological surgery and occurs in two major forms: (1) cancellous bone and (2) cortical bone. Cortical bone is highly dense and has a compound structure comprised of calcium hydroxyapatite reinforced with collagen fibers and is the predominant load bearing component of long bones in the human and animal body. Due to these characteristics, the monolithic body 10 of the intervertebral implant unit is preferably formed from human and/or animal cortical bone.

A bone composite can be composed of bone particles, powder, chips, etc., that are distributed within a binder which may, or may not be bioresorbable. Optionally, a filler material may be incorporated, such as hydroxyapatite and, if desired, one or more biologically active components, medical agents, and/or drugs, as is fully disclosed in co-pending US. Provisional Application Ser. No. 60/254,378 fully incorporated herein by reference.

In order to further improve the biomechanical characteristics of cortical bone, the bone may be strengthened. In particular, the collagen fibers of the initial bone-related materials used for forming the inventive implant unit can be exposed at the surface of the bone and then chemically or mechanically cross-linked with a suitable cross-linking agent or embedded fiber. Collagen fibers can be exposed by demineralizing the bone with a suitable acid. Chemically, a cross linking agent reinforcing exposed collagen fibers can contain multifunctional reactive groups and preferably could contain, but is not limited to, formaldehyde, glutaraldehyde, acetaldehyde, glyoxal pyruvic aldehyde, dialdehyde starch, glycerol polyglycidyl ethers, polyethylene glycol diglycidyl ethers, polyvalent metallic oxides, dicyclohexyl carbodiimide or some combination of these. Mechanically, the exposed collagen fibers can be reinforced by wrapping one or more reinforcing fibers around the bone in a direction perpendicular to the lengthwise orientation of the bone. As a result, the implant unit made up of bone has a high degree of flexibility and exquisite strength.

Following the preparatory stage of the inventive method, transverse cuts are made through the metaphysis or diaphysis of the bone to form a plurality of cortical elements. Depending on the anatomical configuration and dimensions of the host bone, each of the annular elements is further machined to conform to this anatomical configuration by using a milling device or the like. Preferably, the bone is demineralized to reduce the inorganic content of the bone utilizing the defatting/demineralization procedure.

Figure 24:
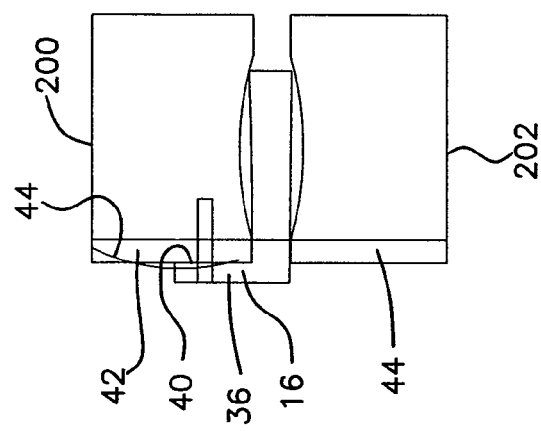
FIG. 24 is a view similar to the one shown in FIG. 23, but formed with a multi-wing retaining portion.
Figure 23:
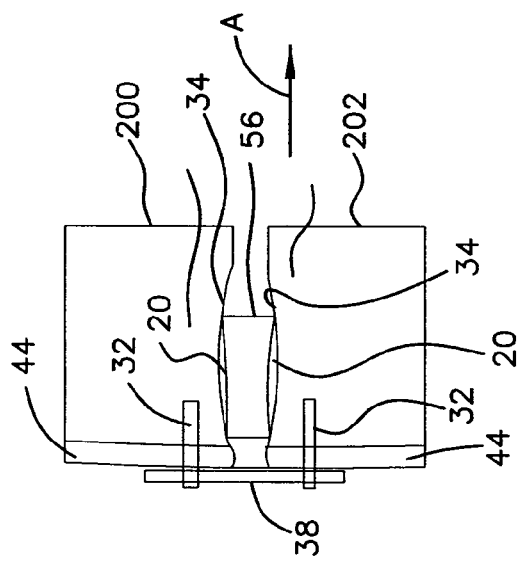
FIG. 23 is a diagrammatic side view of a one-wing retaining portion of the inventive monolithic implant unit.

Referring to FIGS. 5 and 23, 24 the body 10 is machined with the implant portion 12 having generally an arcuate cross-section 24. The arcuate implant portion 12 is formed substantially midway between opposite ends 26 and 28 of the retaining portion 14, which, in this case, is machined as a plate. To ensure alignment of the implant unit with the adjoining vertebrae bodies, the implant portion 12 is dimensioned to fit in an intervertebral space. As can be seen in FIG. 23, after disc removal, the implant portion 12 of the body 10 is placed in the vacated disc space 56 such that surfaces 20 and 22 of the implant portion 12 engage adjacent vertebral endplates 200 and 202. Top and/or bottom surfaces 20 and 22 may be shaped to conform to the natural curvature of the juxtaposed vertebral endplates or to support the vertebrae in a particular orientation, such as a distal end 34 of the endplates, as shown in FIG. 24.

Figure 1A:
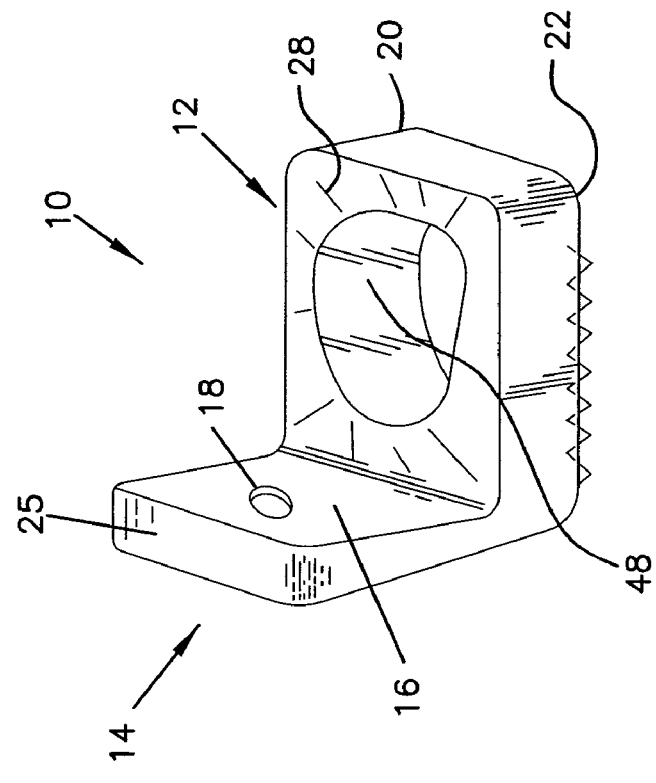
FIGS. 1A-1D is an isometric view of one embodiment of an implant unit manufactured in accordance with the invention.
Figure 8:
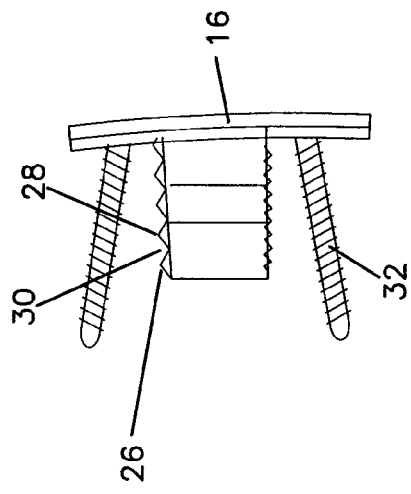
FIG. 8 is a side view of another embodiment of the monolithic implant unit shown in FIGS. 1A-1D.
Figure 7:
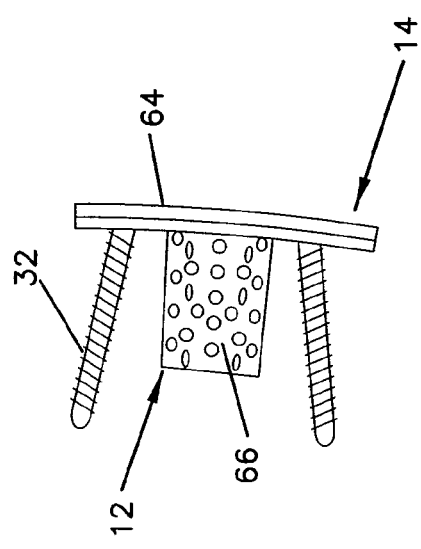
FIG. 7 is a side view of one of the embodiments of the monolithic implant unit shown in FIGS. 1A-1D.

Furthermore, as illustrated in FIG. 1A and FIGS. 7, 8, the opposite surfaces 20, 22 of the implant portion 12 can be serrated, ridged, spiked and/or knurled, as indicated by reference numeral 28. Texturing the opposite surfaces improves biomechanical characteristics of the implant unit. In particular, each pair of adjacent ridges 26, 28 of the textured surface formed on the implant portion 12 defines a respective valley 30 providing an additional contact area during fusion between the implant unit and the adjoining vertebrae bodies.

After the implant portion 12 is positioned in the intervertebral space, a transverse member 16 of the retaining portion 14 is secured to the sidewall of vertebrae by a fastener, such as a screw 32, which extends through hole(s) 18 (FIG. 1A) to fixedly retain the implant body 10 in relation to the adjoining vertebrae. The implant body 10 may be adjusted in the longitudinal and/or lateral directions of the spine. To provide for displacement of the inserted implant body 10 in the desired direction, the holes 18 can have an oblong cross-section allowing for manipulation of the implant body before the screws are tightened. The number of the holes 18 can vary, as well as their shape which can be oval, rectangular and/or other irregular configurations. Optionally, the holes can be made by the surgeon at the time of surgery, and do not need to be initially manufactured into the implant. The fasteners 32 can be made from biocompatible materials including, but not limited to: bone, bone related composites, stainless steel, titanium, ceramics, hydroxyapatite, polymers, carbon fiber, and/or tantalum. It is preferred that the fasteners 32 extend into the adjoining vertebrae at an angle differing from a right angle with respect to the primary retaining surface. In particular, the position in which the fasteners 32 diverge from one another (FIGS. 7, 8) is advantageous, although a converging orientation of the screws could also be implemented.

Figure 3:
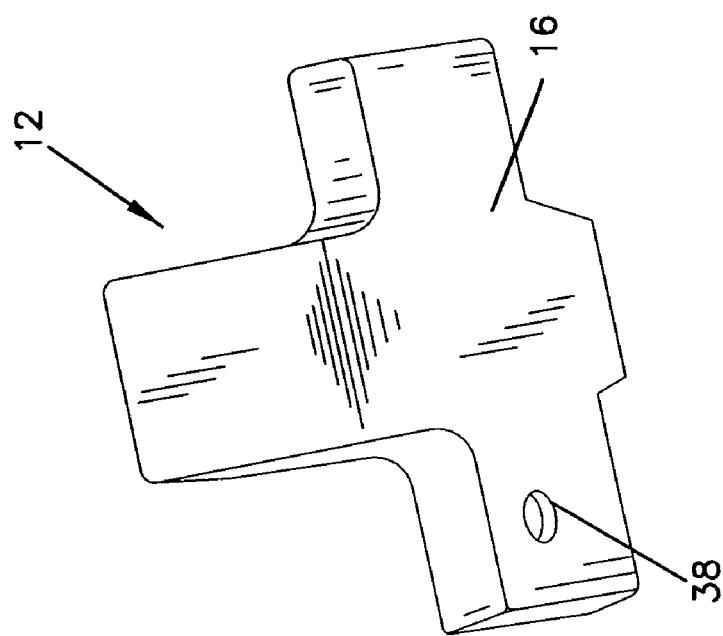
FIG. 3 is a rear view of still another configuration of the monolithic implant unit with a retaining portion formed with offset wings.

The transverse member 16 of the retaining portion 14 can have either a single wing 36 (FIG. 24) or double wing 38 (FIG. 23). The retaining portion 14 provided with a two-wing structure, as shown in FIG. 3, can have the wings 38 extend in parallel planes. Utilization of the transverse member 16 along with the single extending wing 36 is preferred for a multi-level fusion that provides fixation of a plurality of vertebral bodies. A longitudinal face 40 (FIG. 24) of the transverse member 16 facing the sidewall 44 of the adjoining vertebrae can be machined to conform to a curved contour of the vertebra. In particular, the face(s) 40 of the transverse member 16, can have a concave contour ily the convex contour of front sides 42 of the vertebral sidewalls 44.

Figure 1D:
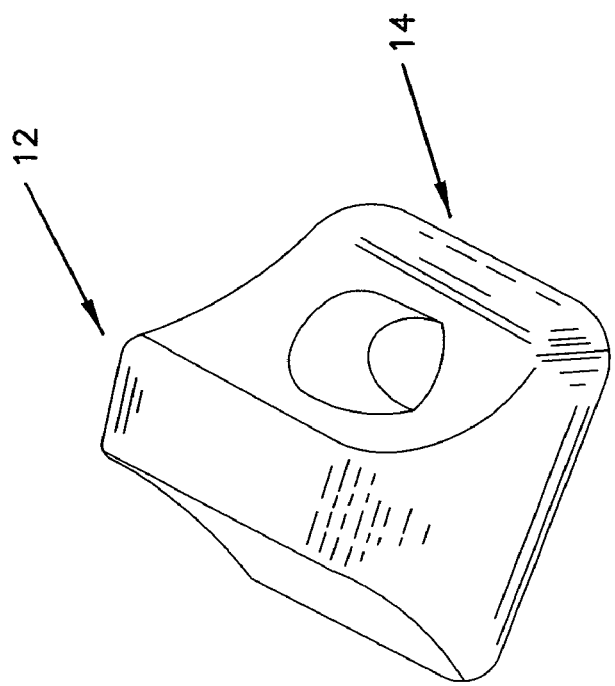
Figure 1B:
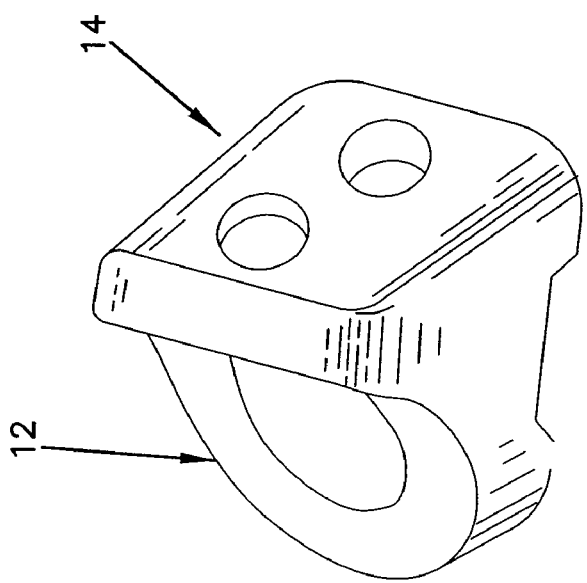
Figure 2:
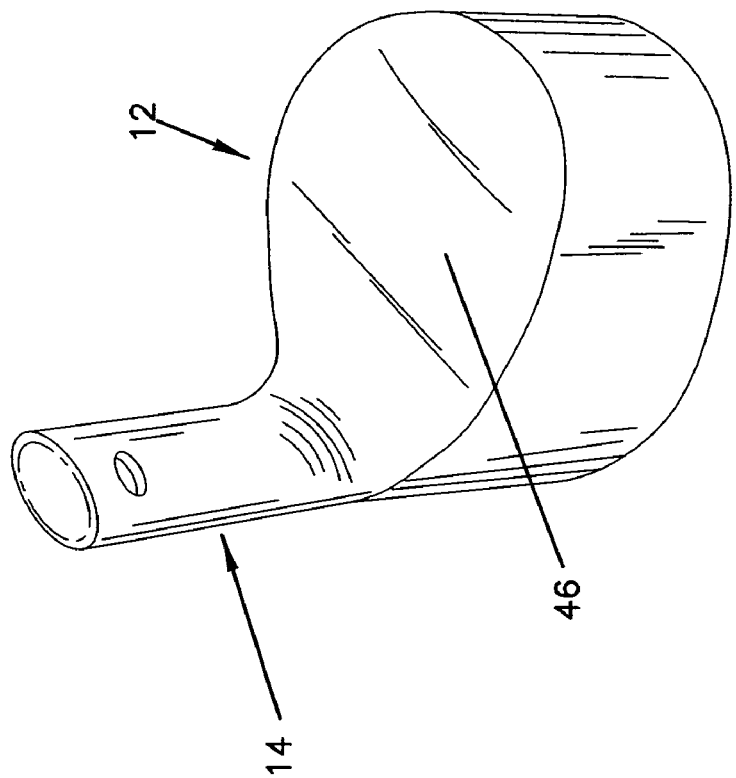
FIG. 2 is is an isometric view of one of the monolithic implant units shown in FIG. 1 and having its medullary canal filled with a filler.
Figure 1C:
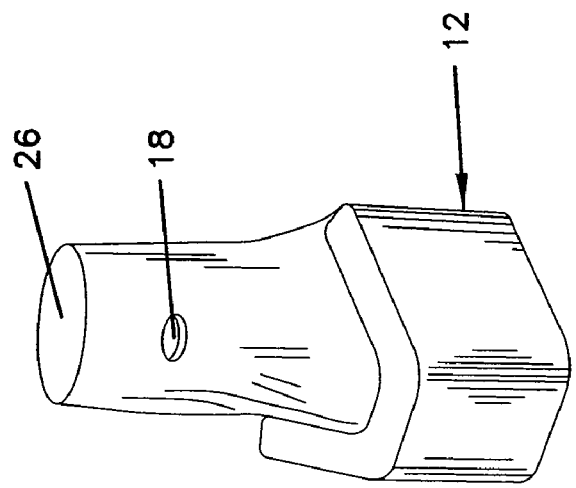
Figure 4B:
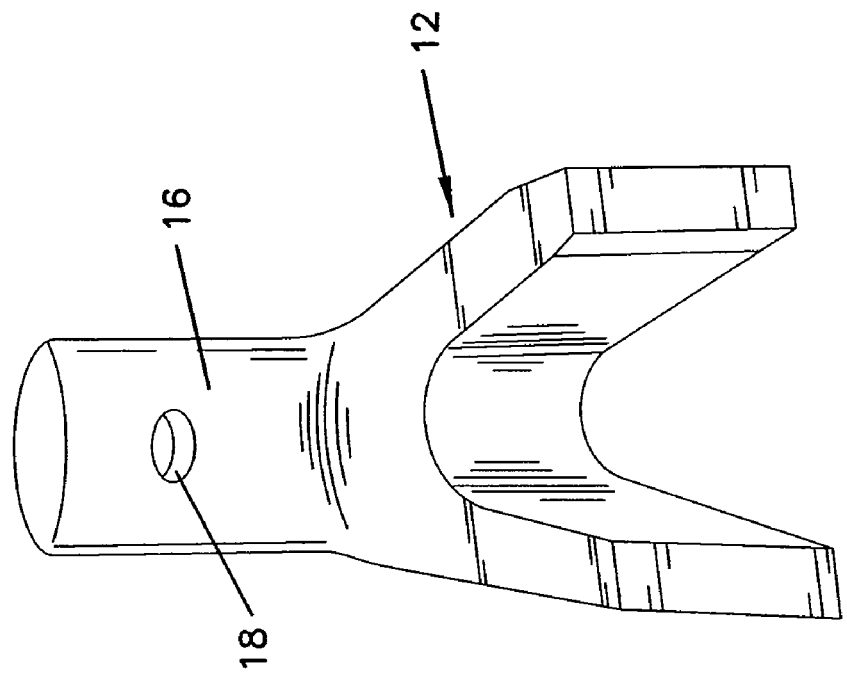
FIGS. 4A-4C are an isometric view of another embodiments of the retaining portion of the inventive monolithic implant unit.

In FIGS. 1B-1D, the implant portion 12 of the monolithic body 10 is dimensioned to be received by the intervertebral space and may assume a variety of different configurations. For example, the implant portion 12 may have a continuous periphery having a rectangular (FIG. 1D), trapezoidally (FIG. 1C) or a U-shape (FIG. 1B). Alternatively, the implant portion 12 can have a discontinuous C-shaped (FIG. 4A) or V-shaped periphery (FIG. 4B). If the intervertebral implant unit is formed from long bones, each implant unit is provided with a through opening or bore 48 of the medullary canal or cavity. As shown in FIG. 2, filling or packing the through bore 48 can be accomplished by inserting a bone plug 46 or by packing the opening with one or more materials or compounds. This will facilitate or accelerate the remodeling, ingrowth and/or repair of the bone. Such materials include demineralized bone matrix, which includes demineralized bone powers and/or fibers or combinations thereof, and other materials that are known to those skilled in this art.

Figure 4C:
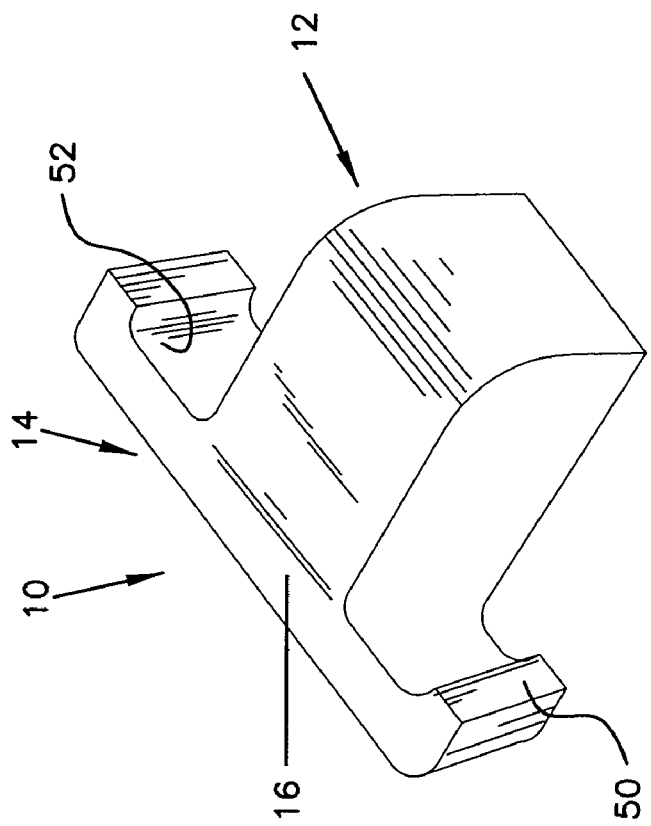
Figure 4A:
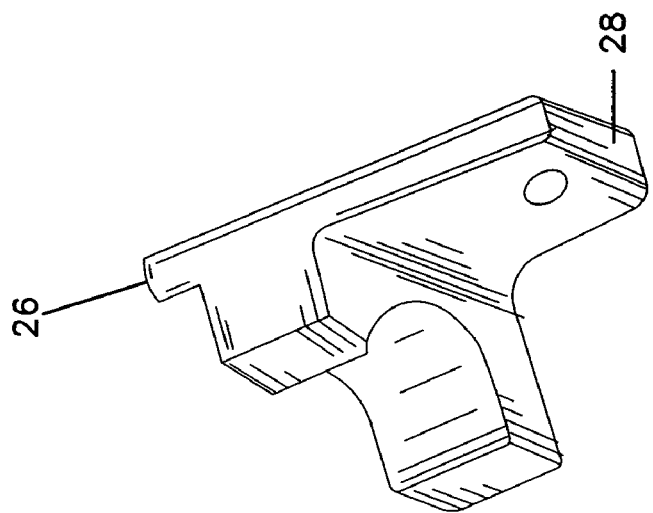
Figure 12:
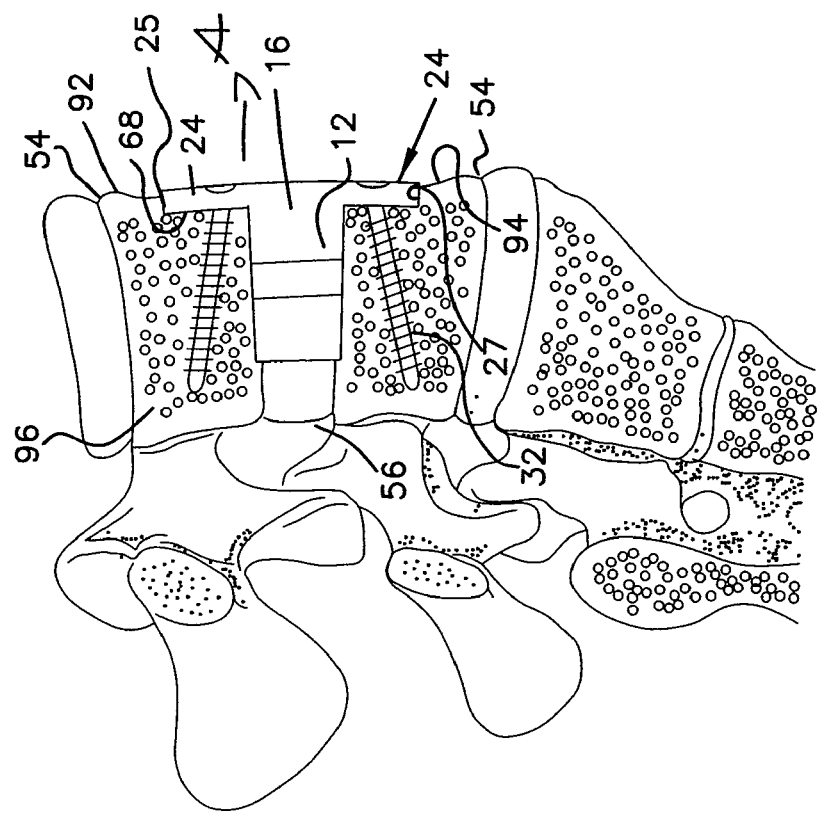
FIG. 12 is a view similar to the one shown in FIG. 11, but featuring the embodiment of the inventive monolithic implant unit of FIG. 8.

Referring to FIG. 4C, the monolithic body 10 has the implant portion 12 and the transverse member 16 and is designed to nest between adjoining vertebrae to be fused in a multilevel fusion procedure. Engagement of the monolithic body 10 with the adjoining vertebral bodies is facilitated by the fasteners 32 and by the opposite ends of the transverse member 16, each having a respective tab 50. The tabs 50 each have a rounded surface 52 extending angularly with respect to the longitudinal direction of the transverse member 16 and embracing the vertebrae's sidewall end regions 54 and further having an end 25, 27 (FIG. 12). As a result, relative displacement of the embraced vertebral bodies and the implant unit in the longitudinal and transverse directions is prevented.

Figure 6:
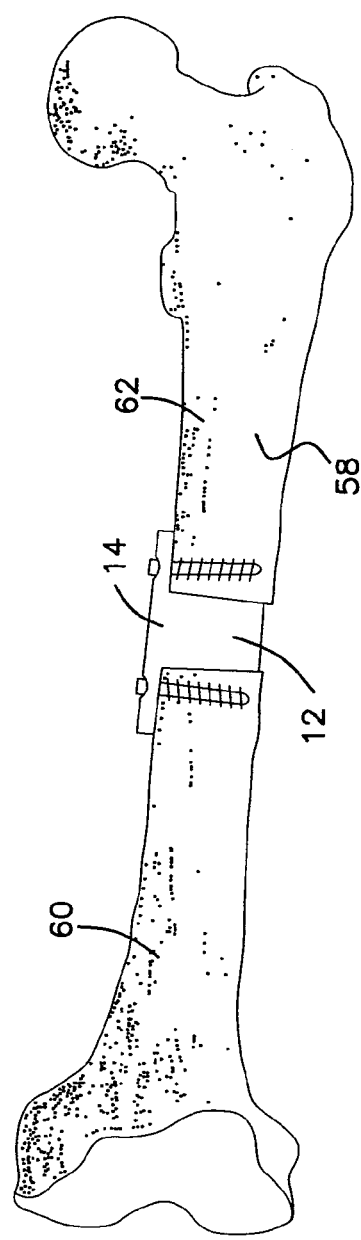
FIG. 6 is a view of a non-union fractured bone treated with the inventive monolithic implant unit shown in FIG. 5.

Although the above-written discussion has been directed primarily to spinal procedures, which apply to the cervical, thoracic, lumbar, and sacral levels, the above disclosed implants are easily adapted to treating a variety of bone defects, deformities, abnormalities and fractures. For example, FIGS. 5 and 6 illustrate an implant unit used for the treatment of a non-union fracture of a long bone 58. The implant unit, as shown in FIG. 5, has a C-shaped implant portion 12 that can be successfully utilized for joining fractured parts 60, 62, which are attached to the retaining portion 14 in a manner described above.

Figure 9:
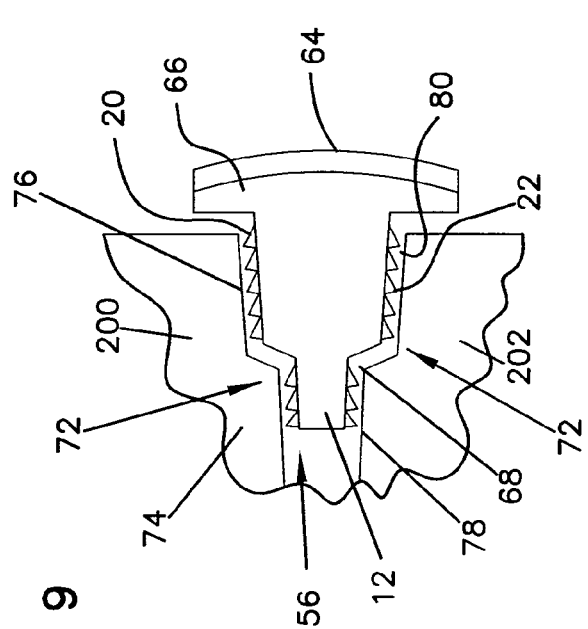
FIG. 9 is a side view of still another embodiment of the monolithic implant unit.
Figure 11:
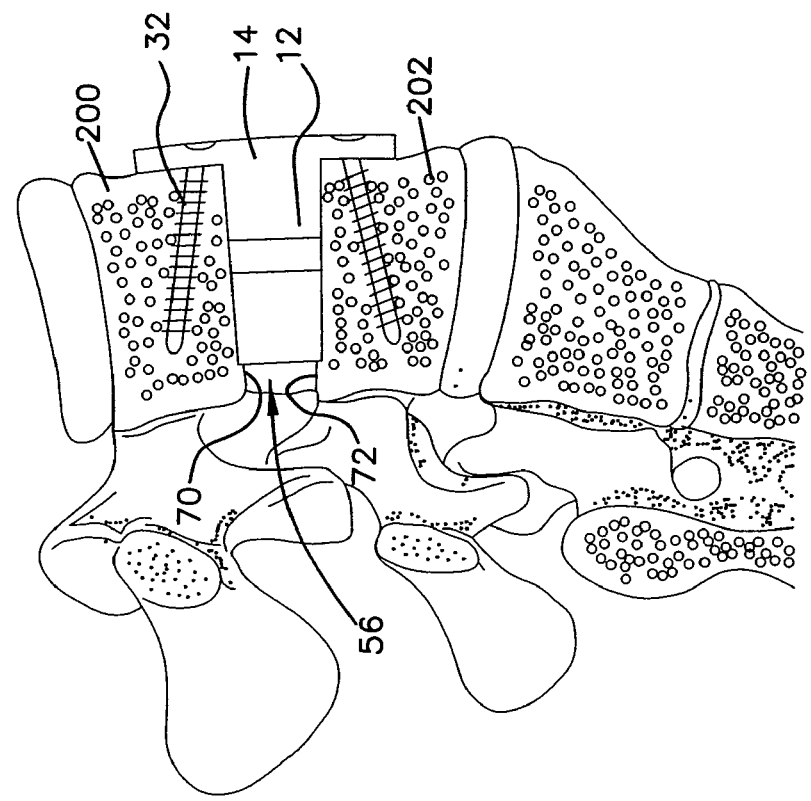
FIG. 11 is a side view of the intervertebral of FIG. 7 utilized in an anterior discectomy of all levels of the spine.

Referring to FIGS. 7 and 11, the monolithic implant body 10 is so formed that the transverse member 16 includes an outer, highly dense cortical layer 64 and an inner, cancellous bone layer 66. Furthermore, as shown in FIG. 9, to accelerate growth of bone into the implant unit, and to provide improved movement restriction, the top 20 and bottom 22 surfaces of the implant portion 12 contain ledges 68 defining a stepwise structure of the implant portion of the implant unit. Accordingly, the inner surfaces 70, 72 of the adjoining vertebrae bodies 200 and 202 also have stepwise structures, which have portions 74, 76, 78 and 80 extending at different levels and pressing against respective surfaces of the implant portion 12.

As shown in FIG. 11, once the intervertebral disc has been partially or fully removed to form a suitable space 56, the adjacent vertebral bodies 200 and 202 are spread apart in a longitudinal direction and supported in this position by a suitable tool. The surgeon, using a scalpel, chisel, curette and/or rasp provides the inner surfaces 70, 72 of the intervertebral space 56 with the desired shaped. Thus, as shown in FIGS. 11 and 12, the inner surfaces 70 and 72 of the vertebrae bodies are substantially flat, and converge toward one another, the intervertebral space 56 having a generally conical shape, narrowing toward the posterior portion of the spine. To provide adjacent vertebral bodies 200 and 202 and the implant portion 12 with improved contact, the height of the implant portion, gradually decreases, and is smallest at the posterior aspect of the implant. Initially, the overall implant portion of the construct is at least equal to, or slightly greater than the distance between the vertebral bodies before they have been spread. Upon removal of the spreading tool, the vertebral bodies apply a compressive load to the implant portion 12.

In case of the stepwise top 20 and bottom 22 surfaces of the implant portion 12, as shown in FIG. 9, the surgeon will form portions 74, 76, 78 and 80 on the inner surfaces 70, 72 of the vertebrae bodies such that they extend into the space 56 at different distances. Accordingly, the inner surfaces 70 and 72 of the adjoining vertebral bodies are shaped and dimensioned to extend complementary to the recessed surfaces of the implant portion 12 and to compress these surfaces after the spreading tool has been removed.

Figure 10:
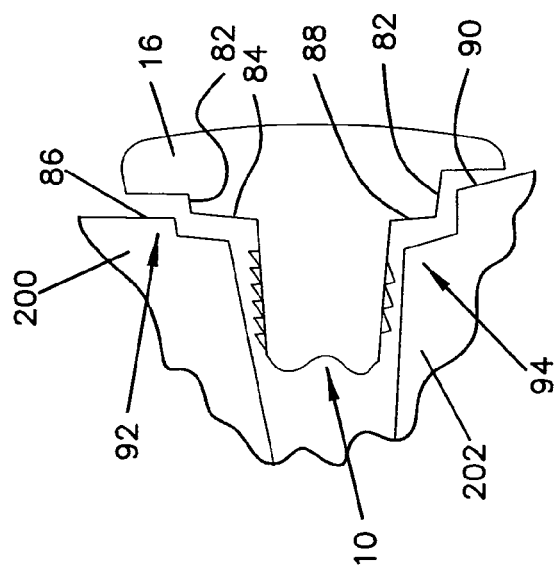
FIG. 10 is side of a further embodiment of the inventive monolithic implant.

Another embodiment of the implant unit is illustrated in FIG. 10 and features the modified retaining portion 14, which has a transverse member 16 formed with a ledge 82. The concept of this embodiment is similar to the one disclosed with respect to FIG. 7 and directed to diminishing loads imposed upon the screws 32. Accordingly, the outer cortical sidewall 92, 94 of the vertebral bodies 200, 202 are recessed so that their rear portions 84, 86, 88 and 90 extend complementary to respective multilevel surfaces of the transverse member 16. Also, the monolithic body 10 shown in FIGS. 8 and 10 is made from a bone composite including, as previously disclosed, bone tissue mixed with a polymer binder.

Whether the transverse member 16 of the implant unit has multi-level inner surfaces, as shown in FIG. 10, or does not, as illustrated in FIG. 8, it is desirable to form a niche in the outer cortical sidewalls 92, 94, which are the strongest part of the vertebral bodies and are typically about 1 to 2 mm thick. FIG. 12 illustrates the rational for recessing the sidewalls 92, 94. The interior 96 of the vertebral body 200, 202 is formed primarily of porous cancellous bone, which is substantially weaker than cortical bone. Ideally, a surgeon will position a vertebral implant between the sidewalls 92, 94 of the adjoining vertebrae bodies so that the implant unit does not extend outwardly beyond these sidewalls. However, because sidewalls 92 and 94 are thin, it may be difficult to maintain the implant body 10 in this position. Even a slight displacement of the implant body not exceeding 1 mm in the direction indicated by arrow "A" into the intervertebral receiving space 56, shifts the implant body 10 so that the weak cancellous bone, which can be easily deformed, now supports the implant body 10. Thus, the transverse member 16 receiving a substantial portion of the vertical load is critical for proper functioning of the implant unit. However, because of the relatively large loads imposed upon the transverse member 16, the screws 32 may not be sufficient to keep the entire unit intact. Recesses formed in the sidewalls 92, 94 and having surfaces, which define a niche 24, provide additional contact areas between the transverse member 16 and the bone sidewalls. As a consequence, part of axial loads is received by these contact areas formed between the peripheral surface of the niche and either the periphery of the transverse member 16, as shown in FIG. 12, or the ledge 82, as illustrated in FIG. 10. Accordingly, the loads carried by the screws 32 are minimized which, in turn, avoids a potential mechanical failure of the transverse member 16 and the screws 32 securing the transverse member to the vertebrae bodies 200 and 202. It is, of course, feasible to combine the embodiment shown in FIGS. 7-10 to even further improve stability of adjoining bone structures.

Figure 13:
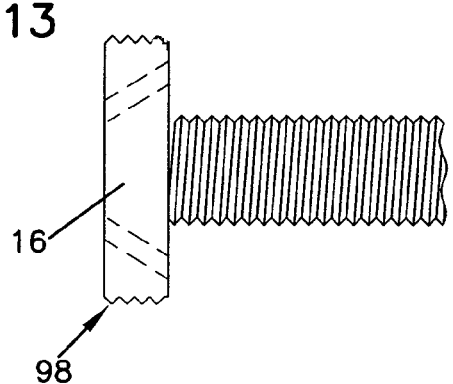
FIG. 13 is a side view of still another embodiment of the monolithic implant unit.
Figure 14:
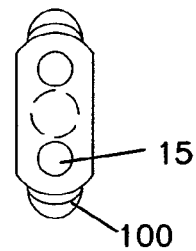
FIG. 14 is a top view of a retaining portion of the implant unit shown in FIG. 13.

FIGS. 13, 14 illustrate a further embodiment of the monolithic implant body 10 providing another configuration of a means for securing the transverse member 16 to the outer cortical sidewalls 92, 94. In addition to the screws 32 fastening the transverse member 16 to the cortical sidewalls, the annular periphery 98 of the transverse member 16 has a thread 100 mating with a respective thread provided in the cortical sidewalls of the vertebral bodies. Again, providing a threaded contact area between the cortical bone and the implant reliably secures the implant unit to the bone and accelerates fusion therebetween.

If the inventive implant is formed with the body 10 assembled of the separate implant 12 and retaining portions 14, it is imperative that attachment between the transverse member 16 and the implant portions 12 be reliable. Embodiments of the inventive implant units illustrated in FIGS. 14-19 are particularly useful for manufacturing an implant assembly including detachably connected implant 12 and retaining 14 portions.

Figure 15:
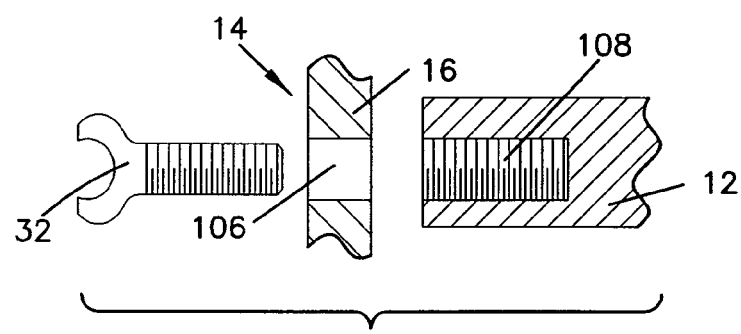
FIG. 15 is an exploded side view of an implant unit provided with detachable retaining and implant portions.

Referring to FIG. 15, an implant assembly has the implant portion 12, which can be either dowel or ramp shaped and have a textured surface, and the retaining portion 14 detachably connected to the implant portion 12. Both portions are provided with holes 106 and 108 aligned with one another upon insertion of the implant portion into the intervertebral space. As the holes are aligned, the screw 32 is inserted into the hole 106 provided in the retaining portion 14 and is further screwed into the blind hole 108 extending substantially along a central axis of the implant portion 12 and having a thread, which mates with the thread provided on the screw 32. Alternatively, a pin shaped and dimensioned so that it can frictionally fit into the holes 106 and 108 can be used as a fastener. Both the screw and the pin can be made from bone, partially demineralized bone, demineralized bone, bioresorbable material or metal.

Figure 16:
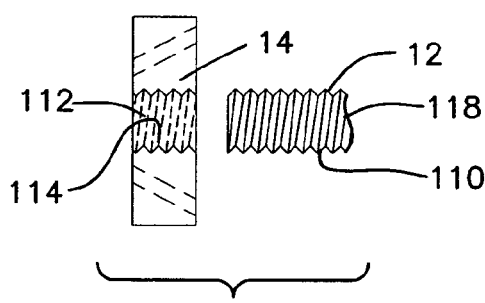
FIG. 16 is an exploded side view of the of another embodiment of the implant unit having detachable implant and retaining portions.
Figure 17:
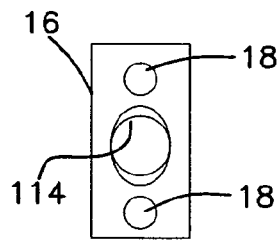
FIG. 17 is a top view of the retaining portion of the implant unit shown in FIG. 16.
Figure 19:
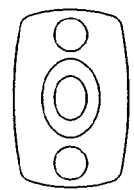
FIG. 19 is a top view of the retaining portion of the implant unit illustrated in FIG. 18.

FIGS. 16-17 show the implant assembly having the implant 12 and retaining 14 portions capable of being detachably coupled together. However, this embodiment has fewer parts than the embodiment illustrated in FIG. 15, since the outer surface of the implant portion has a thread 110 mating with a thread 114 provided on the inner surface of an opening 112, which extends through the transverse member 16 of the retaining portion 14. In general; the implant portion 12 can be cylindrical along its entire length. However, it is possible to provide the threaded proximal end 116 of the implant portion, which engages the transverse member 16, with a circular cross-section while providing the distal end 118 with a different cross-section.

Figure 18:
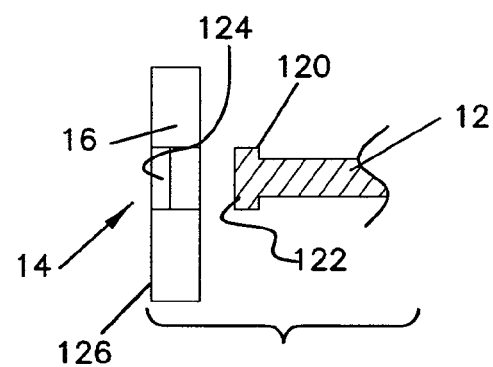
FIG. 18 is an exploded side view of yet another embodiment of the implant unit with detachable retaining and implant portions.

FIGS. 17-18 illustrate another assembly in which the proximal end 120 is capped with a flange 122 extending laterally outwards from the proximal end. The transverse member 16 of the retaining portion 14 has a stepped center hole 124 receiving the flange 122 so that it extends flush with the outer face 126 of the transverse member. The threaded dowel-shaped body is able to pin the retaining portion in a desired position as the implant portion 12 being threaded into the intervertebral space. Accordingly, the threaded dowel-shaped body acts as an additional anchor for the retaining portion 14 along with the screws 32 applied through the retaining portion.

In accordance with the concept of the present invention, the implant assembly illustrated in FIGS. 14-18, particularly the retaining portion 14, can be fabricated from a group of materials including bone composites, cancellous bone, cortical bone, partially or fully demineralized cortical and/or cancellous bone or combinations of these materials.

Optionally, the inventive implant units may also be formed from surgical grade steels such as stainless steel, titanium, polymers, carbon fiber, and tantalum and other biocompatible materials can be used for the manufacturing of the implant unit and assemblies. Methods employed in forming the implant units can include molding, casting or other machining techniques.

As discussed above, each of the intervertebral implant units and assemblies may be segmentally, fully, and/or partially demineralized, especially on the outer surfaces, to improve the osteoinductive characteristics of the implant, or to provide the implant with desired flexibility. By providing the implant with designed areas of flexibility, the implant is able to more easily conform to the shape of the vertebra to which it is adjacent. Moreover, by increasing the osteoinductive characteristics of the implant, the fusion process can be accelerated.

Figure 20:
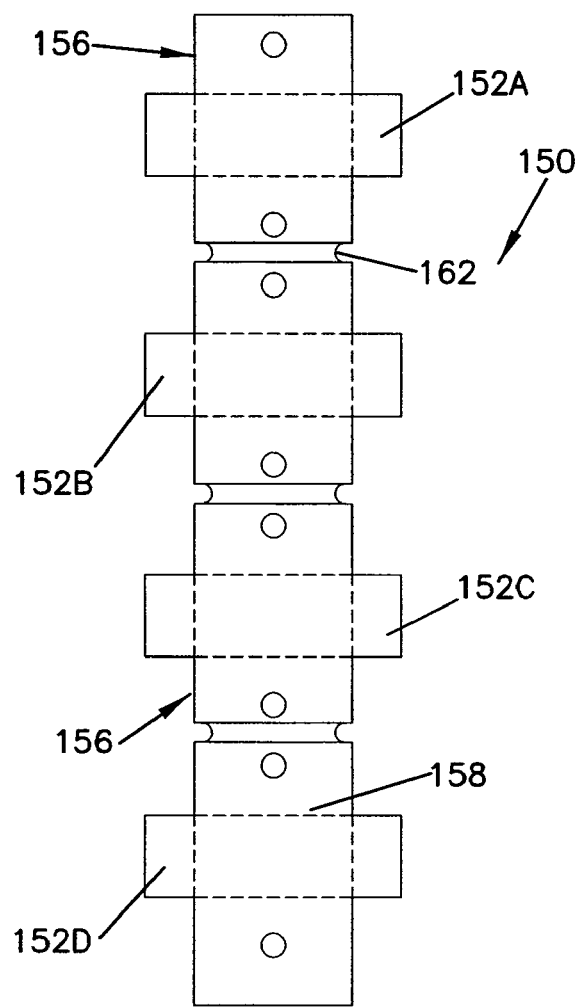
FIG. 20 is a rear view of another embodiment of the multi-section monolithic intervertebral implant unit.
Figure 21:
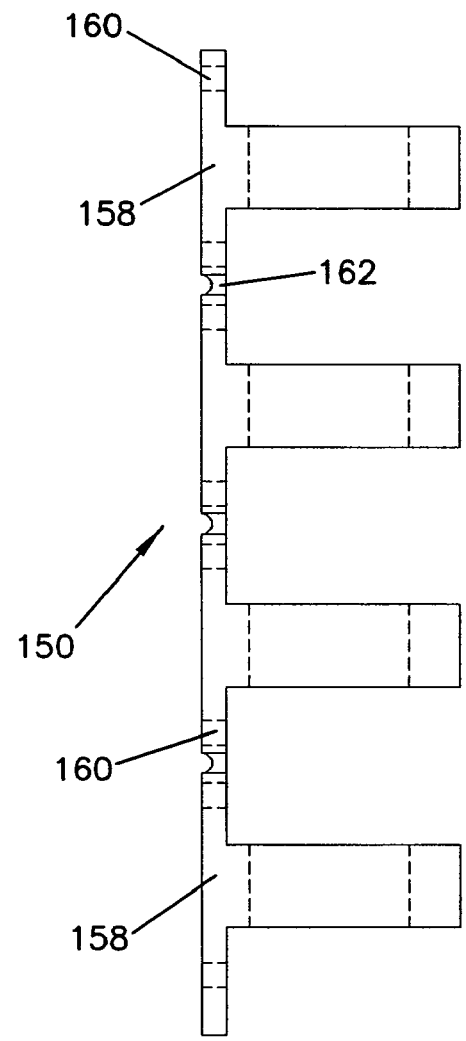
FIG. 21 is a side view of the intervertebral monolithic implant unit shown in FIG. 20.
Figure 22:
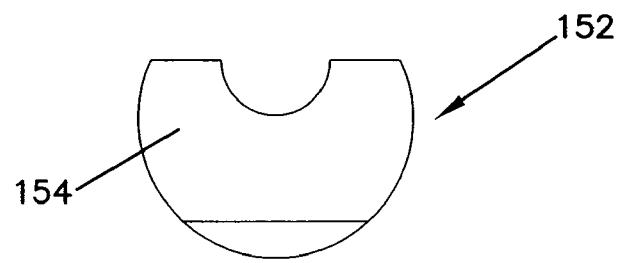
FIG. 22 is a cross-sectional view of the implant portion of the monolithic implant unit shown in FIGS. 20 and 21.

FIGS. 20-22 illustrate an alternate embodiment of the presently disclosed intervertebral implant unit 150. Implant unit 150 is a multi-level implant body, which includes a plurality of sections 152 A-D shaped in accordance with any desired configuration including those illustrated in the previously discussed embodiments. Purely for the illustrative purposes, the sections 152 A-D have a C-shaped implant portion, as illustrated in FIG. 22.

Each section 152 A-D is formed with a monolithic body comprised of an implant portion 154 and a retaining portion 156. In accordance with the concept of the invention, each retaining portion is provided with a transverse member 158, which includes at least one hole 160 for receiving a fastener securing the retaining portion to the sidewall of a vertebra, as discussed above.

A flexible portion(s) 162 interconnects adjacent sections 152 to facilitate the placement of the monolithic intervertebral implant 150 at various positions along the spinal column. As discussed above, the entire implant unit 150 may be formed as a one-piece body from any biocompatible material including those listed above, but is preferably formed from cortical bone. Connecting flexible portions 162 may be partially or fully demineralized to provide the desired degree of flexibility to the implant and are somewhat thinner than the adjoining transverse members of the adjacent sections.

Thus, the inventive implant assembly is advantageous over the known prior art because the mechanical load-bearing configuration of the implant unit is optimized as is the movement resistant structure disclosed herein. Furthermore, forming the inventive implant assembly from the 100% human or animal bone or bone composites enhances fusion between the adjoining bone and the implant unit, which leads to long-term stability that cannot be matched by the bone repaired with metallic implants.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An implant unit for repairing a vertebral segment or segments or a bone repair site in mammalian bone comprising:
   an implant portion for insertion into an intervertebral space or bone repair site extending in an insertion plane and juxtaposed with surfaces to be repaired, the implant portion having a top surface and a bottom surface, wherein the top surface and bottom surface of the implant portion are contoured to complement the surfaces to be repaired; and
   a retaining portion for retaining the implant portion in the intervertebral space or bone repair site, the retaining portion being formed of an osteogenic material and extending in its longest dimension transversely to the insertion plane of the implant portion, being provided on a proximal end of the implant portion, and being attachable to a sidewall of the at least one vertebral body or a mammalian bone, the retaining and implant portions being configured and coupled to one another so that during the period of repair the retaining portion substantially prevents displacement of the implant unit relative to the surface to be repaired and the implant unit carries loads over the intervertebral space or the mammalian bone,
   wherein the implant portion has a flange extending laterally outwards from at least one end of the implant portion, the flange being received in a stepped central opening of the retaining portion and being dimensioned so that the flange extends flush with an outer surface of the retaining portion after the implant unit is inserted into the intervertebral space or bone repair site.

2. The implant unit according to claim 1 wherein the implant portion and the retaining portion are formed from an implantable material comprising bone tissue selected from the group consisting of bone particles, bone powder, bone chips, and/or a combination of these, and/or a bone composite comprising bone tissue distributed in a polymeric binder; and contain at least one osteogenic component, and at least one medical agent and/or drug.

3. A method of using an implant unit for joining spaced vertebral bodies each having an inner face to be fused and a sidewall extending transversely to the inner face, comprising the steps of:
   providing an implant portion comprising implantable biocompatible material;
   providing a retaining portion comprising osteogenic material, the retaining portion being attachable to the sidewall and coupled to a proximal end of the implant portion so that the retaining portion and implant portions extend transversely to one another, wherein the implant portion has a flange extending laterally outwards from at least one end of the implant portion, the flange being received in a stepped central opening of the retaining portion and being dimensioned so that the flange extends flush with an outer surface of the retaining portion after the implant unit is inserted into the intervertebral space or bone repair site;
   recessing a portion of the sidewall to form a niche;
   and positioning the implant unit such that the retaining portion is partially nested within the previously formed niche of the recessed sidewalls to bear loads imposed upon the spine, the retaining portion substantially prevents displacement of the implant unit relative to the surface to be repaired, and the retaining portion extends in its longest dimension transversely to an insertion plane of the implant portion.

4. The method according to claim 3, wherein the implant portion and the retaining portion are formed from an implantable material comprising bone tissue selected from the group consisting of bone particles, bone powder, bone chips, and/or a combination of these, and/or a bone composite comprising bone tissue distributed in a polymeric binder; and contain at least one osteogenic component, and at least one medical agent and/or drug.

5. The method according to claim 3, wherein the implant portion has a thickness greater than the distance between the opposing inner faces defining the intervertebral space.

6. The method according to claim 3, wherein the implant portion is provided with opposing top and bottom surfaces each formed with serrations, ridges, knurling and/or other surface roughening features.

7. The method according to claim 6, wherein at least one of the top and bottom surfaces has a ledge defining a stepwise face extending complementary to the respective adjacent inner face of the surfaces to be fused.

8. The method according to claim 3, wherein the retaining portion has an inner surface facing the sidewalls and having a ledge, wherein the ledge extends generally parallel to the insertion plane of the implant portion and is juxtaposed with an inner surface of the niche formed in the sidewalls of the adjoining vertebral bodies to provide a greater contact area for the transmission of loads.

9. The method according to claim 3, wherein the retaining portion has an outer peripheral surface extending substantially parallel to the insertion plane of the implant portion and supporting the surface which defines the niche provided in the sidewalls of the vertebral bodies.

10. The method according to claim 3, further comprising a plurality of fasteners traversing respective openings formed in the retaining portions and penetrating the sidewall of the adjoining vertebral bodies.

11. The method according to claim 10, wherein each of the openings is so dimensioned that the fasteners are capable of being multi-directionally displaced therein before being fixed to the sidewalls of the adjoining vertebral bodies to provide desired positioning of the implant portion.

12. The method according to claim 3, wherein the implant and retaining portions are detachably coupled.

13. An implant unit for joining spaced vertebral bodies each having an inner face to be fused and a sidewall extending transversely to the inner face, wherein at least the sidewalls have been recessed to form a niche, the implant unit comprising:
    an implant portion extending in an insertion plane and into the intervertebral space and being interposed between the inner faces following discectomy, wherein a height of the implant portion gradually decreases and wherein the implant portion has a truncated conical portion narrowing in a posterior direction; and
    a retaining portion comprising osteogenic material, the retaining portion being attachable to the sidewall, being coupled to a proximal end of the implant portion, and extending in its longest dimension transversely to the insertion plane of the implant portion and shaped to engage the recessed sidewalls, wherein the retaining portion is configured to substantially prevent displacement of the implant unit relative the surface to be repaired, the retaining portion being so dimensioned that upon insertion of the implant portion into the intervertebral space, the retaining portion is at least partially nested within the niche of the recessed sidewalls to bear loads imposed upon the spine;
    wherein the implant portion has a flange extending laterally outwards from at least one end of the implant portion, the flange being received in a stepped central opening of the retaining portion and being dimensioned so that the flange extends flush with an outer surface of the retaining portion after the implant unit is inserted into the intervertebral space or bone repair site.

14. The implant unit according to claim 13, wherein the implant portion has a thickness greater than the distance between the opposing inner faces defining the intervertebral space.

15. The implant unit according to claim 13, wherein the implant portion is provided with opposing top and bottom surfaces each formed with serrations, ridges, knurling and/or other surface roughening features.

16. The implant unit according to claim 13, wherein the implant portion is provided with opposing top and bottom surfaces and wherein at least one of the top and bottom surfaces has a ledge defining a stepwise face extending complementary to the respective adjacent inner face of the surfaces to be fused.

17. The implant unit according to claim 13, wherein the implant portion is provided with opposing top and bottom surfaces and wherein at least one of the top and bottom surfaces is contoured to complement a surface to be repaired.

18. The implant unit according to claim 13, wherein the implant portion and the retaining portion are formed from an implantable material comprising bone tissue selected from the group consisting of bone particles, bone powder, bone chips, and/or a combination of these, and/or a bone composite comprising bone tissue distributed in a polymeric binder.

19. The implant unit according to claim 18, wherein the implant portion and the retaining portion further comprise at least one osteogenic component, and at least one medical agent and/or drug.

20. The implant unit according to claim 13, wherein the retaining portion has an inner surface facing the sidewalls and having a ledge, wherein the ledge extends generally parallel to the insertion plane of the implant portion and is juxtaposed with an inner surface of the niche formed in the sidewalls of the adjoining vertebral bodies to provide a greater contact area for the transmission of loads.

21. The implant unit according to claim 13, wherein the retaining portion has an outer peripheral surface extending substantially parallel to the insertion plane of the implant portion and supporting the surface which defines the niche provided in the sidewalls of the vertebral bodies.

22. The implant unit according to claim 13, further comprising a plurality of fasteners traversing respective openings formed in the retaining portions and penetrating the sidewall of the adjoining vertebral bodies.

23. The implant unit according to claim 22, wherein each of the openings is so dimensioned that the fasteners are capable of being multi-directionally displaced therein before being fixed to the sidewalls of the adjoining vertebral bodies to provide desired positioning of the implant portion.

24. The implant unit according to claim 13, wherein the implant and retaining portions are detachably coupled.

* * * * *